United States Patent [19]

Maglinte

[11] Patent Number: 5,242,395
[45] Date of Patent: * Sep. 7, 1993

[54] BALLOON DECOMPRESSION CATHETER

[75] Inventor: Dean D. T. Maglinte, Zionsville, Ind.

[73] Assignee: Cook Incorporated, Bloomington, Ind.

[*] Notice: The portion of the term of this patent subsequent to May 14, 2008 has been disclaimed.

[21] Appl. No.: 605,651

[22] Filed: Oct. 30, 1990

Related U.S. Application Data

[63] Continuation of Ser. No. 340,922, Apr. 20, 1989, Pat. No. 5,015,232.

[51] Int. Cl.5 .............................................. A61M 25/00
[52] U.S. Cl. .................................... 604/96; 604/264; 606/194
[58] Field of Search ............................ 604/96–102, 604/39, 41, 43, 264, 280; 606/191, 192, 194

[56] References Cited

U.S. PATENT DOCUMENTS

| | | | |
|---|---|---|---|
| 2,470,665 | 5/1949 | Stiehl | 128/276 |
| 2,930,378 | 3/1960 | Buyers | 604/96 |
| 3,527,203 | 9/1970 | Gravlee | 128/2 |
| 4,114,625 | 9/1918 | Onat | 128/348 |
| 4,364,394 | 12/1982 | Wilkinson | 604/96 |
| 4,579,554 | 4/1986 | Glassman | 604/102 |
| 4,596,563 | 6/1986 | Pande | 604/280 |
| 4,642,092 | 2/1987 | Moss | 604/43 |
| 4,676,778 | 3/1987 | Nelson, Jr. | 604/101 |
| 4,715,848 | 12/1987 | Beroza | 604/35 |
| 4,917,667 | 4/1990 | Jackson | 604/264 |
| 5,015,232 | 5/1991 | Maglinte | 604/96 |

OTHER PUBLICATIONS

"Ring—McLean Sump Drainage Sets", Cook®*Diagnostic and Interventional Products* 1986.
Maglinte DT, "Small Bowel Radiography: How, When, and Why?", Radiology 1987; 163:297–305.

*Primary Examiner*—C. Fred Rosenbaum
*Assistant Examiner*—C. Smith
*Attorney, Agent, or Firm*—Woodard, Emhardt, Naughton, Moriarty & McNett

[57] ABSTRACT

This invention relates to a catheter useful in examination of the small bowel which incorporates three lumens and a balloon and can thus prevent reflux of infused fluid as well as clear obstructions of the infusion ports.

22 Claims, 2 Drawing Sheets

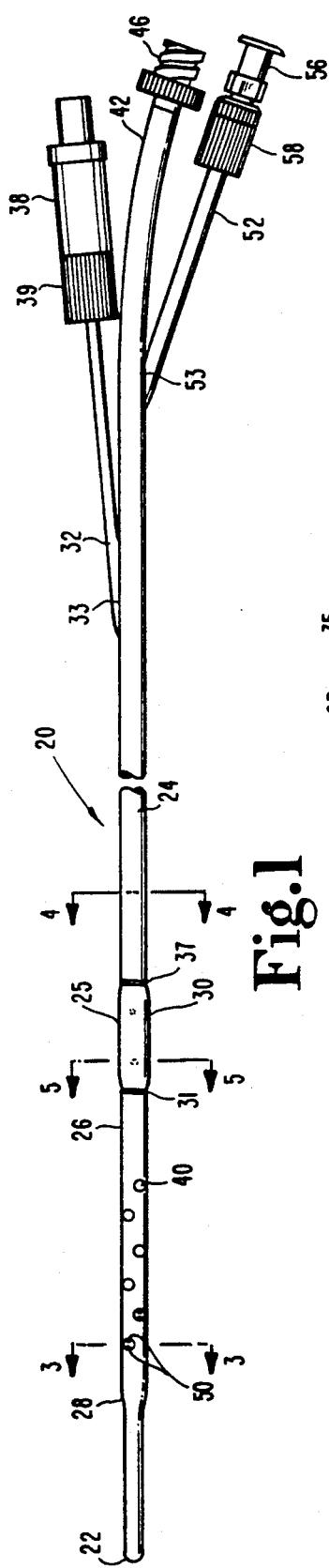
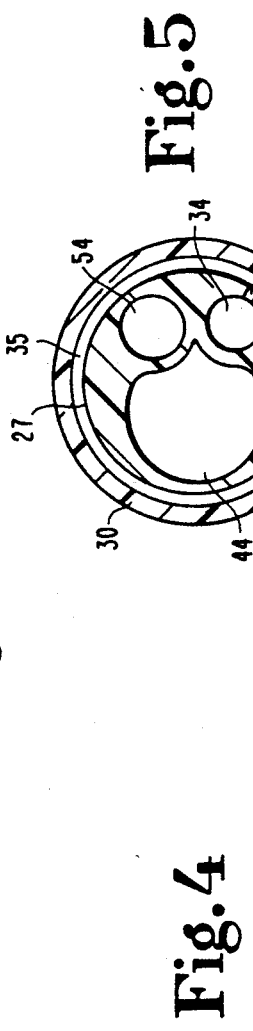
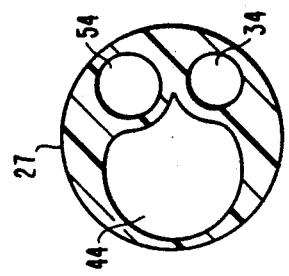
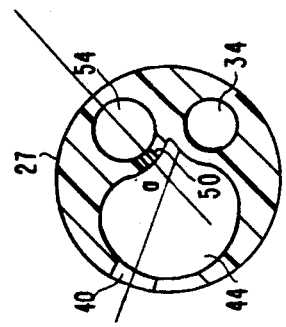
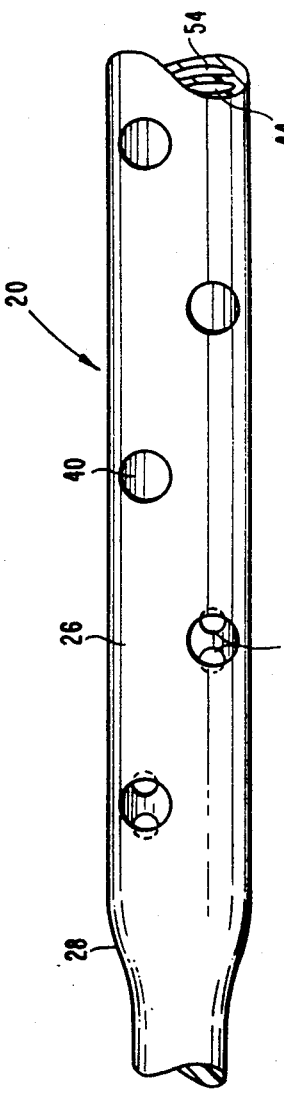

BALLOON DECOMPRESSION CATHETER

This application is a continuation of application Ser. No. 340,922, filed Apr. 20, 1989, now U.S. Pat. No. 5,015,232.

BACKGROUND OF THE INVENTION

1. Field of the Invention

This invention relates generally to a decompression catheter, which might find application, for example, in small bowel enteroclysis.

2. Brief Description of the Background

Oral methods are often advantageous in the medical examination of the small bowel, mainly due to the ease of performance. In this regard, enteroclysis is often considered a preferred oral method for examining the small bowel for irregularities, as it overcomes some of the interpretive and technical errors present in other oral methods.

Enteroclysis presents several practical and diagnostic advantages. Accordingly, this oral method has been used to successfully diagnose a wide variety of lesions. One advantage of enteroclysis over other oral methods of evaluating the small bowel is that it bypasses the regulation of the stomach and pylorus. Also, contrast material may be delivered at a preselected optimized rate. Further, direct infusion of the contrast material into the small bowel achieves simultaneous demonstration of all loops in the distended bowel. Thus, fold patterns are more accurately evaluated and surface abnormalities may show up more definitely. An additional advantage of enteroclysis is that the examination may be performed in a relatively short period of time.

It has been suggested that a catheter ideal for performing enteroclysis should incorporate certain features. It must be long enough to reach the infusion site and still allow the patient freedom to shift positions during the infusion. The diameter of the enteroclysis catheter should be minimized so that irritation to the nasopharyngeal or oropharyngeal tracts is minimized. Provision for preventing reflux of the infusion material into the stomach or decompressing refluxed contrast material in the stomach is advantageous. See, Maglinte D. T., *Small Bowel Radiography: How, When, and Why?*, Radiology 1987; 163:297–305. The decompression catheter of the present invention supplies all the above features. Importantly, it incorporates an additional feature. Frequently, the infusion ports of enteroclysis catheters become obstructed with body tissue or other material, making further injection or withdrawal impossible. Thus, the additional feature is one which clears obstructed ports of the catheter so that injection or withdrawal may proceed.

Previously available small bowel decompression catheters are typically double-lumen catheters. These catheters take time to position in the proximal small bowel for effective decompression. In addition, the immediate performance of enteroclysis to ascertain the site and severity of the obstruction is not possible as these catheters are not adapted for contrast infusion into the bowel. When contrast media is injected, backflow into the stomach occurs because of the position of the holes in the end of the catheter.

The decompression catheter of the present invention, designed with a triple-lumen and incorporating a balloon, can be readily positioned directly in the proximal small bowel for effective decompression. It is adapted also for immediate enteroclysis for determination of the site and severity of obstruction or other diagnostic and intervention procedures. Further, a double sump is present which enables clearing of the infusion or withdrawal ports. Also, the distal portion may be tapered to minimize nasopharyngeal or oropharyngeal irritation during insertion.

Several drainage and/or irrigation devices are presently known. None, however, are well-suited for oral examination of the small bowel. Wilkinson, U.S. Pat. No. 4,364,394, discloses a combined sump drainage and irrigation device for evacuating liquid, blood or exudate from the peritoneal cavity for prolonged periods. The device incorporates a balloon to prevent dislocation of the device from the incision and a means to aid in equalizing pressure, inhibiting blockage of the suction passage. An infusion passage extends well beyond the distal end of the device's main body.

Onat, U.S. Pat. No. 4,114,625, teaches an oral-nasal gastric tube which includes three passages, one for inflating a balloon. The remaining two tubes open independently external of the device. One tube may be left open to the atmosphere to equalize pressure within the body.

Moss, U.S. Pat. No. 4,642,092, discloses a gastrointestinal aspirating device insertable through the body wall to prevent abdominal distension which frequently occurs when providing nutrition. Primary and smaller, secondary orifices are present in the aspirating lumen so that, should the primary orifices become blocked, the secondary orifices allow a pressure increase (a decrease in the level of suction) within the aspirating lumen.

A Ring-McLean sump drainage set, useful in draining abscesses, is also available. It is introducable by direct puncture from a trochar needle disposed therein. A secondary lumen allows pressure equalization at the distal tip of the catheter or flushing of the primary lumen via a syringe attachment.

None of the above devices disclose the principle of the present invention. That is, none disclose a catheter ideal for use in oral small bowel medical examinations.

SUMMARY OF THE INVENTION

The present invention provides a multi-lumen catheter incorporating a balloon inflatable through one of the lumens. Two remaining lumens communicate internally of the catheter through staggered lateral ports. The paired, smaller ports of the smaller remaining lumen open internally of the catheter into the largest lumen and are aligned with the ports of the larger remaining lumen. The catheter according to this embodiment has a tapered distal portion.

It is an object of the present invention to provide an improved decompression catheter which can be readily positioned in the proximal small bowel for effective decompression.

It is another object to provide a decompression catheter adapted for immediate enteroclysis to determine the site and severity of small bowel obstruction.

It is a further object of the present invention to provide a new and improved decompression catheter incorporating a feature for maintaining patency during enteroclysis.

A further object of the present invention is to provide a decompression catheter capable of aspirating refluxed fluid from the stomach.

A still further object of the present invention is to provide a catheter which is acceptable to the patient during intubation.

Another object of the present invention is to provide a decompression catheter which prevents reflux of contrast media into the stomach.

Further objects and advantages will become apparent from the following description.

BRIEF DESCRIPTION OF THE DRAWINGS

FIG. 1 is a side, plan view of a decompression catheter with balloon according to the preferred embodiment of the present invention.

FIG. 2 is an enlarged, fractional plan view of a portion of the catheter of FIG. 1 taken distal of the balloon.

FIG. 3 is an enlarged cross-section of the catheter of FIG. 1 taken along line 3—3 and looking in the direction of the arrows.

FIG. 4 is a cross-section of the catheter of FIG. 1 taken along line 4—4 and looking in the direction of the arrows.

FIG. 5 is a cross-section of the catheter of FIG. 1 taken along line 5—5 and looking in the direction of the arrows.

DESCRIPTION OF THE PREFERRED EMBODIMENT

Figure 6:
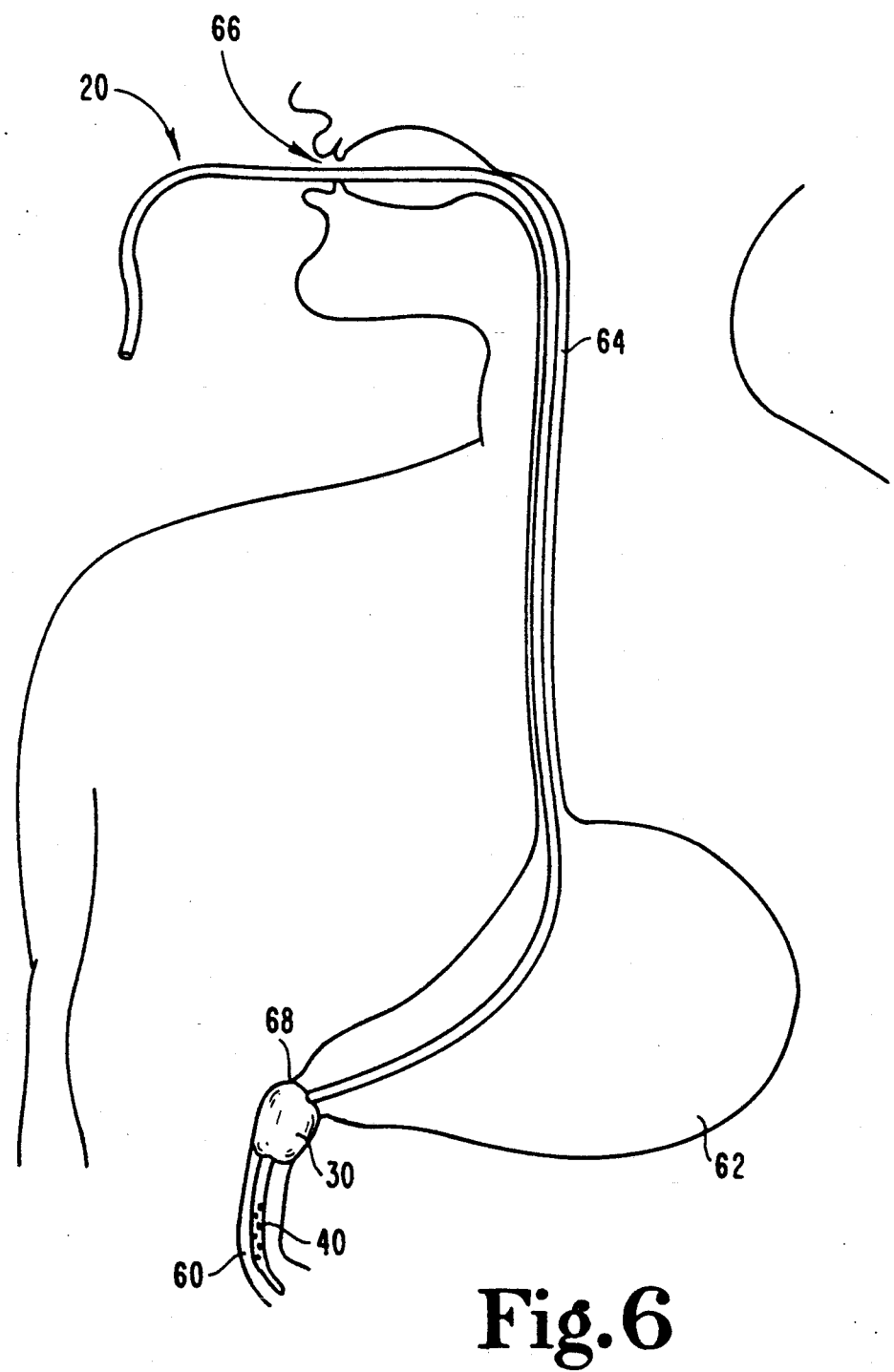
FIG. 6 is a schematic showing a decompression catheter of the present invention inserted through a patient's oral cavity.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more specifically to the drawings, FIG. 1 shows a flexible, tubular catheter 20. Catheter 20 may be typically formed by extrusion, with subsequent treatments resulting in three functionally different portions 24, 25 and 26. Internally, catheter 20 defines three passages 34, 44, and 54. Each of the passages is proximally in communication with an external tube and fixture, and each passage terminates in the distal portion 26.

Balloon 30 is annularly disposed about portion 25 of catheter 20 and is sealingly fixed to portion 25 at proximal end 37 and distal end 31. In general, balloon 30 may be of latex but other materials may also be appropriate. Balloon 30 defines a lumen 35 overlying the outer surface 27 of catheter 20 and underlying the balloon 30. The balloon 30 and its lumen 35 are longitudinally coextensive, extending approximately 2.2 cm. At the proximal end 37 and the distal end 31 the balloon is bound to surface 27, such as with mercerized cotton thread or the like.

Passage 34 provides for inflation of balloon 30. Passage 34 extends through catheter 20 terminating blindly in distal portion 26. Opening laterally and underlying balloon 30, two ports 36 are present in portion 25. These ports 36, approximately 0.035 inches in diameter, are located internally of balloon 30 and communicate between passage 34 and the balloon's lumen 35. Inflation fluid may exit passage 34 at ports 36, inflating the balloon 30.

Tube 32 is connected with portion 24 of catheter 20 and communicates through a hole 33 with passage 34. Passage 34 is sealed proximally of hole 33. From hole 33 to the distal tip 22, catheter 20 is approximately 160 cm. long, more or less. Tube 32 may be a cannula, and preferably is approximately 7 cm. long, ending proximally in a cap 39 and check valve assembly 38 combination. Check valve assembly 38 is secured in fluid communication with tube 32, and is designed so that when in the open position fluids may pass through it into and from balloon inflation passage 34 via tube 32 for inflating and deflating balloon 30. Once the balloon 30 is inflated to the desired diameter and pressure, the check valve assembly 38 may be shut to close access to tube 32 and passage 34 so that the balloon inflation pressure remains constant. A standard check valve assembly 38 and cap 39 may be used.

The distal most portion of catheter 20 is portion 26, terminating in a blunt distal tip 22. The diameter of tip 22 is approximately uniform for a nominal 3 cm. proximal the distal tip, and the diameter gradually increases thereafter at taper 28 where it then continues approximately uniform substantially throughout the length of catheter 20. The decreased diameter and taper 28 provides better patient acceptance during intubation. A cannula (not shown) may be inserted in the distal tip of the catheter 20 for stiffening the tip to facilitate steering the catheter into the small bowel 60.

Portion 26 includes two internal passages 44 and 54. Passage 44 is the larger of the two and opens externally of the catheter 26 via side ports 40. These side ports 40 are staggered to help prevent tissue blockage during use. Present for a nominal 3 cm. proximal of taper 28, side ports 40 are approximately 0.070 inches in diameter. Passage 44 is continuous throughout the length of catheter 20 proximal of taper 28. A standard screw cap fitting 46 is preferably connected with passage 44 at proximal end 42. Thus, a receptacle of contrast media or other material for infusion (not shown) may be connected to screw cap fitting 46 for injection into the small bowel 60 through passage 44. The media enters the small bowel 60 through ports 40. Alternatively, screw cap 46 may be connected to suction to decompress the small bowel 60.

The smaller passage 54 runs beside passage 44 and is similarly continuous. It is proximally in communication with tube 52. Tube 52 ends proximally in fitting 58 having a Luer type connector 56 for the connection of an air supply, suction source or the like (not shown). Passage 54 is provided with side ports 50 which communicate with passage 44. These side ports 50, about 0.035 inches in diameter, are of smaller diameter than side ports 40 and are paired. Catheter 20 is provided with two such pairs corresponding with the two most distal side ports 40. These smaller side ports 50 enable a flushing and/or withdrawal of the bolus after flushing in order to clear any blockage of side ports 40 that results during aspiration of or infusion into the small bowel 60.

FIG. 2 shows a partial, enlarged, plan view of catheter 20 of the embodiment in FIG. 1. The arrangement of side ports 50 as they relate to side ports 40 is shown. Fluid passing through passage 54 exits side ports 50, enters passage 44 and exits catheter 20 through side ports 40. This creates a pressure change at port 40 which sufficiently dislodges any blockage of port 40, enabling the medical procedure to continue. In addition, the injected fluid may be withdrawn through side ports 50 and out of the small bowel 60 through passage 54. Injection through passage 54 followed by withdrawal of the injected bolus, if desired, effectively flushes passage 44.

FIG. 3 is a cross-section of catheter 20 taken through line 3—3 of FIG. 1 and looking in the direction of the arrows further demonstrating the relation of side ports 50 with side ports 40. In the present embodiment the side ports 50 from the smaller passage 54 are not arranged coaxially with the larger passages 40 from passage 44. Instead the central axes of these side ports 40 and 50 intersect at an obtuse angle a.

FIG. 4 is a cross-section of catheter 20 taken along line 4—4 in FIG. 1. Infusion passage 44 is typically of larger diameter than sump channel 54 which, in turn, may be larger than balloon inflation passage 34.

FIG. 5 is a cross-section of catheter 20 taken along line 5—5 in FIG. 1, demonstrating ports 36 as they communicate between passage 34 and lumen 35. Inflation fluid exits passage 34 through ports 36. The fluid enters the balloon's lumen 35 to expand the balloon material in conventional fashion.

In FIG. 6 a catheter 20 according to the present invention is shown positioned for small bowel enteroclysis. The catheter is inserted into the body, for example, through the oral cavity 66, down the esophagus 64, through the stomach 62, past the pyloric sphincter 68 and into the small bowel 60. The balloon 30 is shown inflated from a source of fluid (not shown) to block reflux of infused fluid into the stomach. The appropriate fluid, contrast media in the case of enteroclysis, is then infused from an infusion fluid source (not shown) in communication with passage 44 via screw cap fitting 46. The media exits side ports 40, creating relative hypotonia and filling the loops of the bowel 60.

During the filling, or upon withdrawal of fluid from the small bowel 60 subsequent to examination, the side ports 40 may become partially blocked with tissue or other material present. This blockage prevents or hinders further infusion or withdrawal. To remove the obstruction the ports 40 may be flushed with saline or the like. The saline, for example, is injected through passage 54, entering the larger passage 44 through ports 50. This creates positive relative pressure through the ports 40 sufficient to push the blockage away. Alternatively, the saline dilutes the blockage so that it is less viscous and may be withdrawn when the saline bolus is pulled back through passage 44 with suction. Thereby catheter 20 is flushed, and the medical procedure may resume. Moreover, if the blockage causing material is part of small bowel 60 tissue then damage to such tissue is averted by the preceding method.

Once the subject medical procedure is completed, the balloon 30 may be deflated by opening the stopcock 38. After balloon 30 deflation, the catheter 20 is removed from the body via the oral cavity 66.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A catheter for decompression enteroclysis comprising:
   an elongated flexible tube having a closed distal end and a longitudinal axis along its length;
   a first passage running internally of said flexible tube, said first passage having first lateral ports opening outwardly through said flexible tube at a number of longitudinal locations along said tube; and
   a second passage disposed side by side and outside of said first passage internally of said flexible tube, said second passage having second lateral ports opening only inwardly of said flexible tube into said first passage, each of said second lateral ports being aligned with a corresponding one of the outwardly opening first lateral ports of said first passage at a corresponding one of said number of longitudinal locations.

2. The catheter of claim 1 wherein said first passage and said second passage have proximal ends having means for removable connection to a source of injection fluid and a source of fluid for flushing, respectively.

3. The catheter of claim 1 wherein the said catheter is tapered distal of the lateral ports.

4. The catheter of claim 1 wherein each of said outwardly opening first lateral ports lies longitudinally parallel but not in line with the outwardly opening first lateral port immediately adjacent.

5. A catheter for decompression enteroclysis comprising:
   an elongated flexible tube having a closed distal end and a longitudinal axis along its length;
   a first passage running internally of said flexible tube, said first passage having first lateral ports opening outwardly through said flexible tube at a number of longitudinal locations along said tube;
   a second passage adapted for infusion and withdrawal therethrough of liquid and disposed side by side and outside of said first passage internally of said flexible tube, said second passage having second lateral ports opening only inwardly of said flexible tube into said first passage, each of said second lateral ports being aligned with a corresponding one of the outwardly opening first lateral ports of said first passage at a corresponding one of said number of longitudinal locations;
   an inflatable balloon bladder disposed medially about said flexible tube and having two ends, both of said ends being sealed to said tube to allow inflation of said balloon bladder; and
   a third passage also disposed within said flexible tube and having a distal end communicating within said balloon bladder, said third passage being for inflating said balloon bladder.

6. The catheter of claim 5 wherein said first passage and said second passage have proximal ends having means for removable connection to a source of injection fluid and a source of fluid for flushing, respectively.

7. The catheter of claim 5 wherein the said catheter is tapered distal of the lateral ports.

8. The catheter of claim 5 wherein said third passage has a proximal end having second means for removable connection to a source for inflating said balloon bladder, said proximal end also including means for sealing off the flow to and backflow from said balloon bladder.

9. The catheter of claim 1, wherein each of said second lateral ports of said second passage have an opening area substantially smaller than the opening area of said outwardly opening first lateral ports of said first passage.

10. The catheter of claim 1 wherein:
said outwardly opening first lateral ports of said first passage have a first axis perpendicular to said longitudinal axis of said tube; and
said second lateral ports of said second passage have a second axis perpendicular to said longitudinal axis of said tube,
wherein said first axis defines an angle with respect to said second axis about said longitudinal axis greater than 90° but substantially less than 180°.

11. The catheter of claim 1, wherein said flexible tube includes a flexible tip between said distal end and said first lateral ports of said first passage.

12. The catheter of claim 11, wherein at least said first passage extends through said flexible tip and terminates adjacent said closed distal end.

13. The catheter of claim 5, wherein said flexible tube, said first passage and said second passage are integrally formed.

14. The catheter of claim 5, wherein each of said second lateral ports of said second passage have an opening area substantially smaller than the opening area of said outwardly opening first lateral ports of said first passage.

15. The catheter of claim 5 wherein:
said outwardly opening first lateral ports of said first passage have a first axis perpendicular to said longitudinal axis of said tube; and
said second lateral ports of said second passage have a second axis perpendicular to said longitudinal axis of said tube,
wherein said first axis defines an angle with respect to said second axis about said longitudinal axis greater than 90° but substantially less than 180°.

16. The catheter of claim 5, wherein said flexible tube includes a flexible tip between said distal end and said first lateral ports of said first passage.

17. The catheter of claim 16, wherein at least said first passage extends through said flexible tip and terminates adjacent said closed distal end.

18. The catheter of claim 5, wherein said flexible tube, said first passage, said second passage and said third passage are integrally formed.

19. A decompression enteroclysis catheter for engagement within a body cavity comprising:

an elongated tube having a closed distal end and defining a longitudinal axis along its length;
an infusion passage extending through said tube, said infusion passage having infusion ports opening outwardly therefrom through said tube;
means at a proximal end of said infusion passage for engaging a source of fluid to be infused into the body cavity;
means for clearing said infusion ports of blockage including;
a second passage extending through said tube exterior to said infusion passage;
a plurality of lateral ports, at least a portion of one each of said plurality of lateral ports being at the same location along said longitudinal axis as at least a portion of a corresponding one of said infusion ports and communicating only between said infusion passage and said second passage; and
means at a proximal end of said second passage for engaging a source of fluid to be directed under pressure through said lateral ports toward said infusion ports to clear said infusion ports of blockage; and
inflatable means, connected to said tube between a proximal end of said tube and said infusion ports, for engaging within and closing the opening of the body cavity to support said tube within the body cavity.

20. The enteroclysis catheter of claim 19, wherein:
said infusion ports have a first axis perpendicular to said longitudinal axis; and
said lateral ports have a second axis perpendicular to said longitudinal axis,
wherein said first axis of said infusion ports and said second axis of said lateral ports at substantially the same longitudinal location as said infusion ports intersect at an angle greater than 90° but substantially less than 180°.

21. The enteroclysis catheter of claim 19, further comprising:
means for guiding said tube through the body passageway, including a flexible tip between said closed distal end of said tube and said infusion ports.

22. The enteroclysis catheter of claim 21, wherein said infusion passage extends into said flexible tip.

* * * * *